United States Patent [19]
Schalk

[11] Patent Number: 6,142,980
[45] Date of Patent: Nov. 7, 2000

[54] MULTI-FUNCTION MEDICAL CONTROL VALVE ASSEMBLY

[75] Inventor: Stephen E. Schalk, Walworth, Wis.

[73] Assignee: 3-T Medical Products, LLC, Bloomfield Hills, Mich.

[21] Appl. No.: 09/268,212

[22] Filed: Mar. 15, 1999

[51] Int. Cl.$^7$ ..................................................... A61M 5/00
[52] U.S. Cl. ........................ 604/247; 604/118; 604/119; 604/129; 604/246; 137/512.3
[58] Field of Search ................................... 604/118, 119, 604/246, 247, 311, 129; 137/512.3, 493.7, 493.9, 526

[56] References Cited

U.S. PATENT DOCUMENTS

| | | |
|---|---|---|
| 4,379,470 | 4/1983 | Reutter .................................. 137/493.8 |
| 4,502,502 | 3/1985 | Krug ..................................... 137/512.3 |
| 4,642,097 | 2/1987 | Siposs . |
| 4,671,786 | 6/1987 | Krug . |
| 4,725,266 | 2/1988 | Siposs . |
| 4,758,224 | 7/1988 | Siposs . |
| 5,401,255 | 3/1995 | Sutherland et al. . |
| 5,419,366 | 5/1995 | Johnston . |
| 5,707,356 | 1/1998 | Paul . |

Primary Examiner—Wynn Wood Coggins
Assistant Examiner—Eric Kline
Attorney, Agent, or Firm—Harness Dickey & Pierce P.L.C.

[57] ABSTRACT

The invention is directed to a multi-function control valve assembly for use in aspirating the left ventricle of the heart during open heart bypass surgery. The control valve assembly includes a housing assembly which defines an inlet adapted for connection to a suction tube inserted into the left ventricle and an outlet adapted for connection to a pump. The control valve assembly further includes a valving arrangement that is operable to provide three distinct functions. First, the control valve assembly includes a unidirectional flow valve which is operable to only permit fluid to flow from the inlet to the outlet, thereby preventing a reverse flow situation. Second, the control valve assembly includes a positive pressure relief valve which is operable to vent the outlet when the pressure therein exceeds a predetermined positive pressure value. Third, the control valve assembly includes a vacuum relief valve which is operable to draw ambient air into the outlet when the pressure therein exceeds a predetermined negative pressure value. As an additional feature, the vacuum relief valve is adjustable for permitting the predetermined negative pressure value to be selectively regulated.

14 Claims, 4 Drawing Sheets

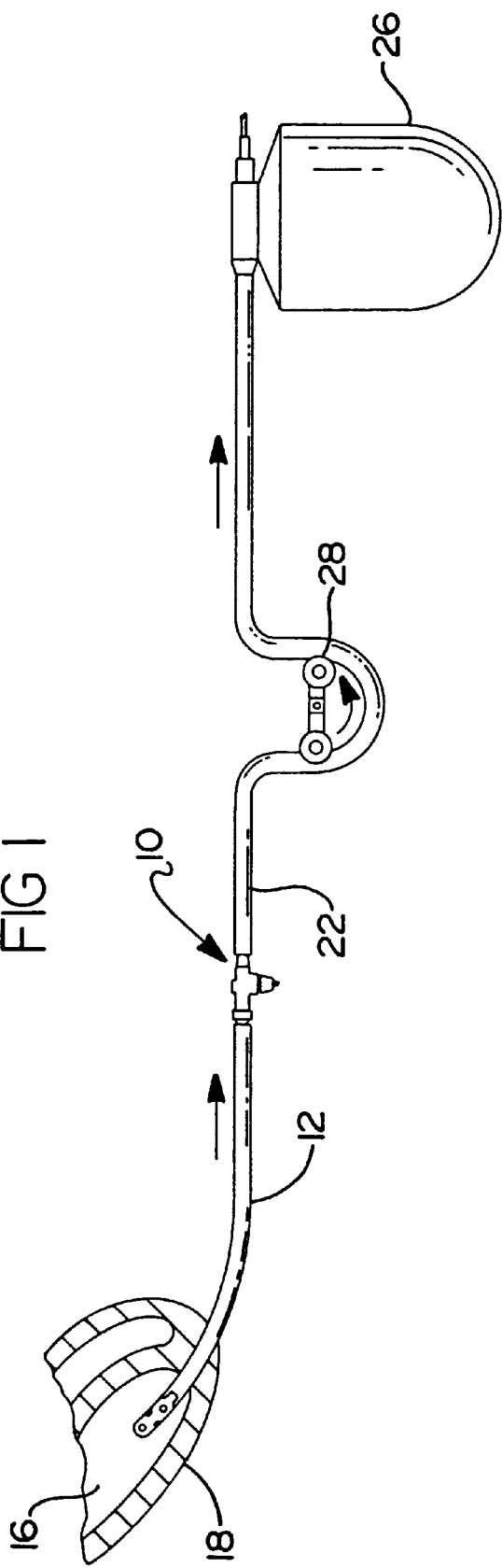
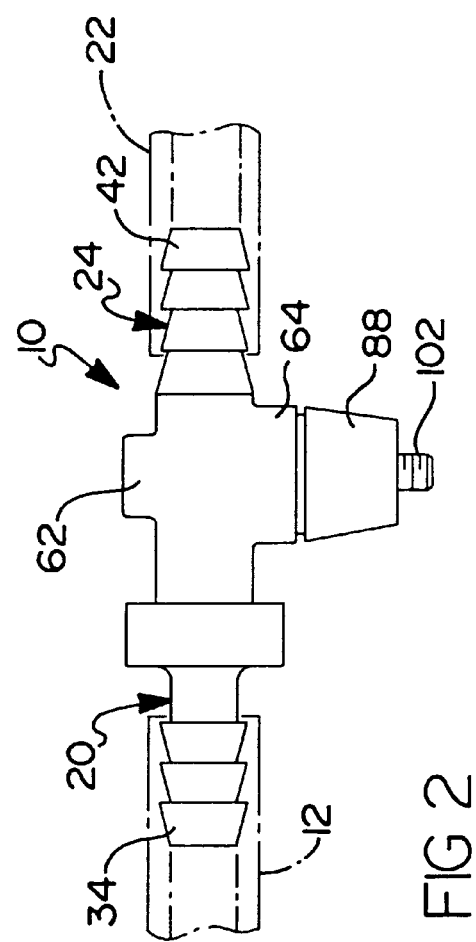

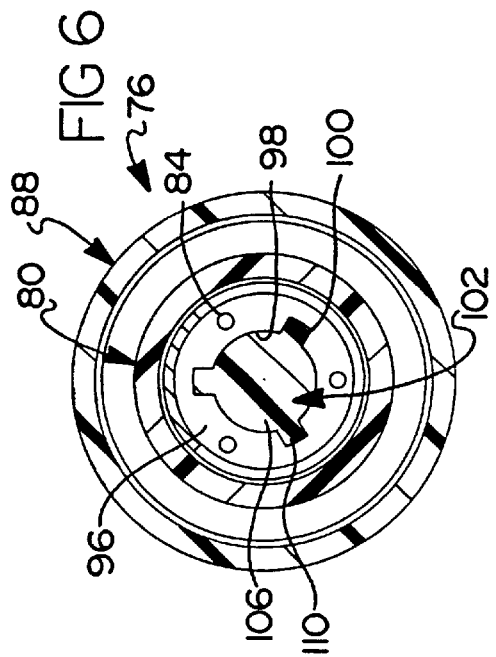
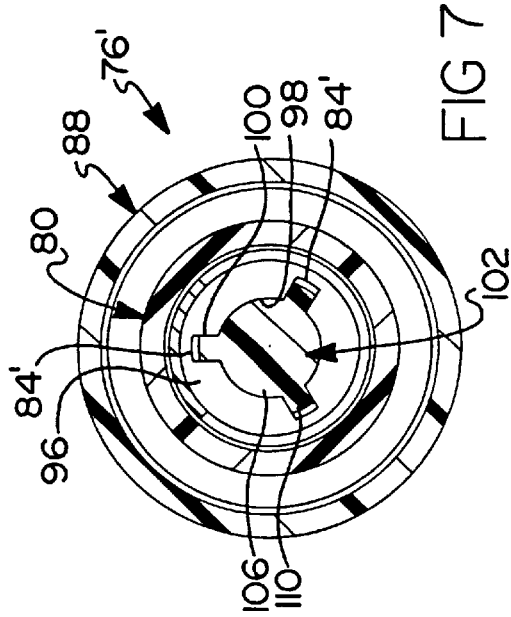
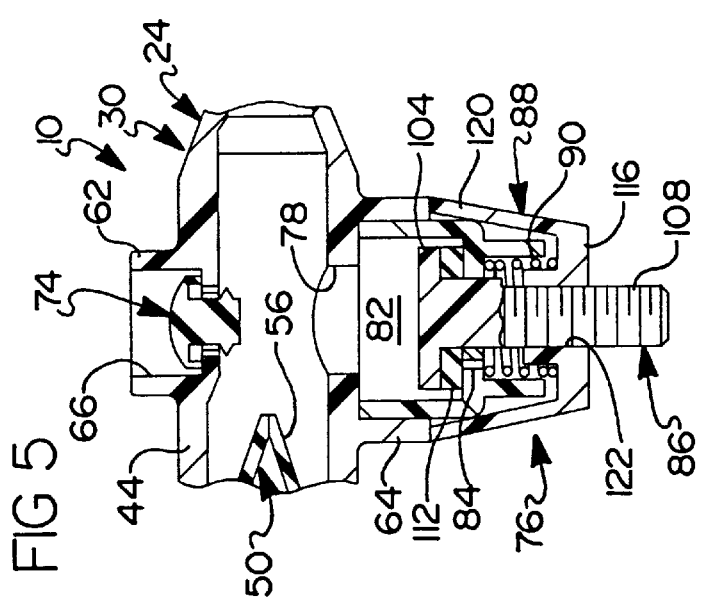

MULTI-FUNCTION MEDICAL CONTROL VALVE ASSEMBLY

BACKGROUND OF THE INVENTION

The present invention is directed to a multi-function control valve assembly for use during open heart surgery to control aspiration of fluid from the left ventricle of the heart.

During open heart surgery, the heart is typically bypassed and the patient's blood circulation is maintained by a heart-lung machine. Moreover, it has been recognized that certain advantages can be gained by decompressing the left ventricle during cardiopulmonary bypass procedures. As such, a drainage tube is inserted into the left ventricle and a pump is used to generate suction for aspirating accumulated blood. To provide means for controlling the rate of aspiration, it is known to install a control valve in the drainage tube between the left ventricle and the pump. In many instances, the control valve functions as a one-way check valve to prevent reverse flow of blood back into the left ventricle in addition to providing both positive and negative pressure relief functions. The positive pressure relief function of the control valve acts to relieve pressure buildups between the pump and the outlet of the control valve. In contrast, the negative pressure relief function of the control valve acts to limit the vacuum pressure in the drainage tube to a desired level. Examples of conventional control valves are disclosed in U.S. Pat. Nos. 4,502,502, 4,642,097, 4,671,786, 4,725,266, 4,758,224, 5,401,255 and 5,707,352. However, despite the existence of such control valves, a need exists to continue development of advanced valving systems which improve upon the art.

SUMMARY OF THE INVENTION

The invention is directed to a multi-function control valve assembly for use in aspirating the left ventricle of the heart during open heart bypass surgery. The control valve assembly includes a housing assembly which defines an inlet adapted for connection to a suction tube inserted into the left ventricle and an outlet adapted for connection to a pump. The control valve assembly further includes a valving arrangement that is operable to provide three distinct functions. First, the control valve assembly includes a unidirectional flow valve which is operable to only permit fluid to flow from the inlet to the outlet, thereby preventing a reverse flow situation. Second, the control valve assembly includes a positive pressure relief valve which is operable to vent the outlet when the pressure therein exceeds a predetermined positive pressure value. Third, the control valve assembly includes a vacuum relief valve which is operable to draw ambient air into the outlet when the pressure therein exceeds a predetermined negative pressure value. As an additional feature, the vacuum relief valve is adjustable for permitting the predetermined negative pressure value to be selectively regulated.

In addition to the variable adjustment feature, the vacuum relief valve can be selectively manipulated during surgery to provide a "dump" feature and a "full vacuum" feature. The dump feature can be selectively actuated to permit ambient air to be drawn into the outlet when the pressure therein is below the predetermined negative pressure value. In contrast, the full vacuum feature can be selectively actuated to prevent ambient air from being drawn into the outlet when the pressure therein exceeds the predetermined negative pressure value. As such, these features allow the vacuum level to be momentarily reduced or increased in a manner independent of the adjustment feature.

BRIEF DESCRIPTION OF THE DRAWINGS

In order to appreciate the manner in which the advantages and objects of the invention are obtained, a more particular description of the invention will be rendered by reference to a specific embodiment thereof which is illustrated in the appended drawings. Understanding that these drawings only depict a preferred embodiment of the present invention and are not therefore to be considered limiting in scope, the invention will be described and explained with additional specificity and detail through the use of the accompanying drawings in which:

FIG. 1 is a circuit diagram showing the control valve assembly of the present invention in its typical use environment of an operating room during open heart surgery;

FIG. 2 is a side elevational view of the control valve assembly according to the present invention;

FIGS. 3 through 5 are sectional views of the control valve assembly showing components of the vacuum relief valve in various operative positions;

FIG. 6 is a sectional view of the control valve assembly taken generally along line X—X of FIG. 3; and FIG. 7 is a sectional view, similar to FIG. 6, showing a modified version of control valve assembly.

DETAILED DESCRIPTION OF THE PREFERRED EMBODIMENT

Figure 3:
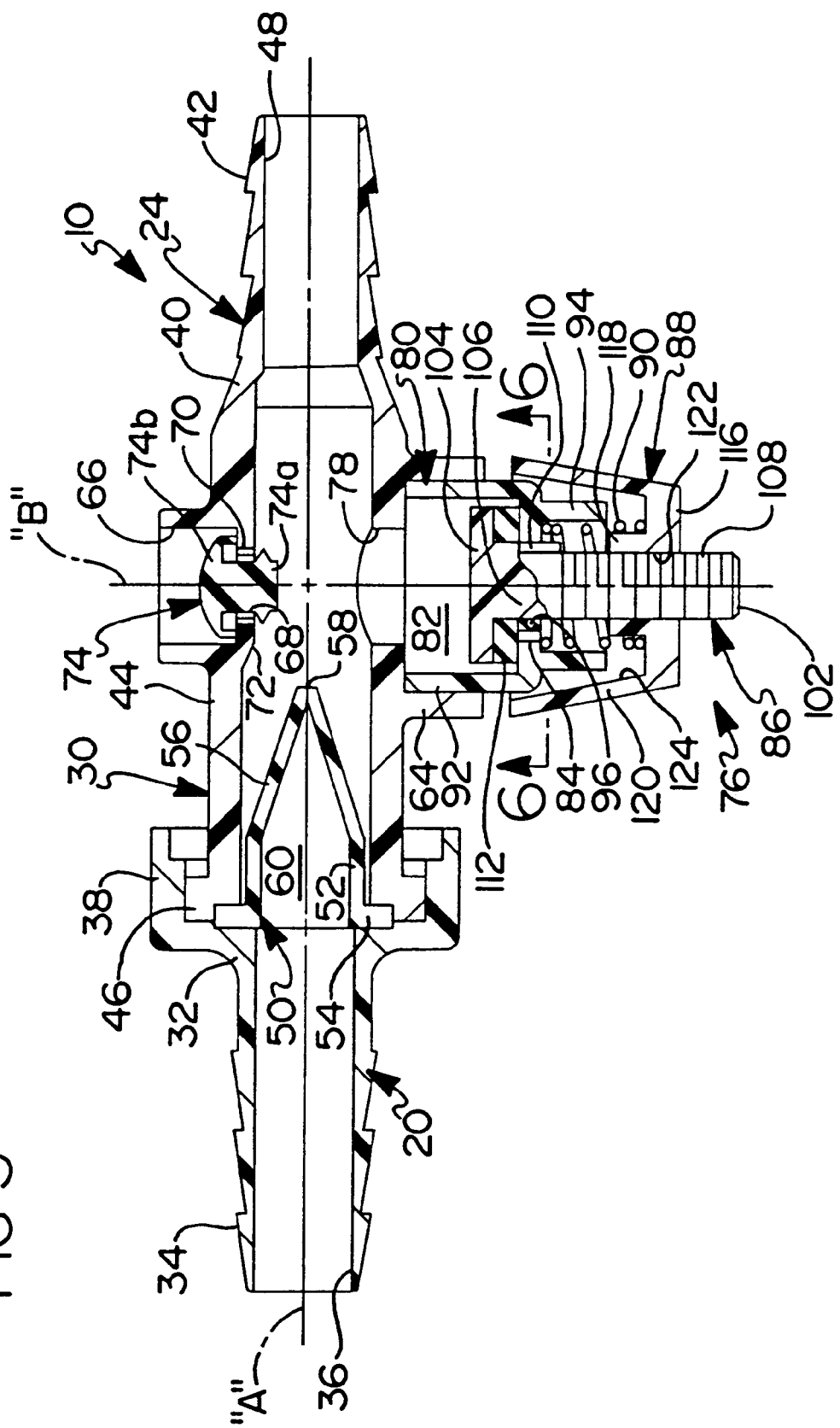
Figure 4:
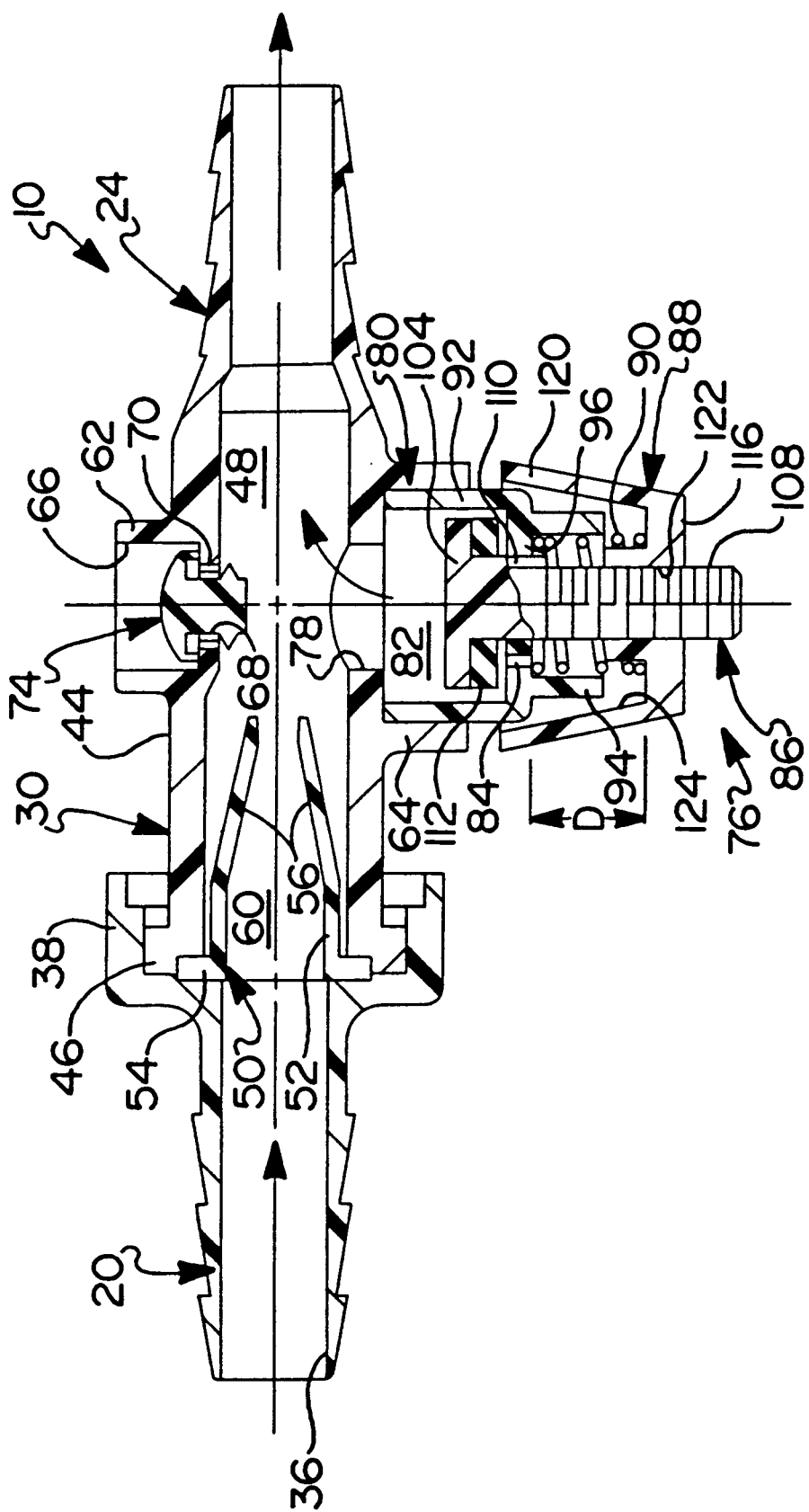

With reference to the drawings, a multi-function control valve assembly 10 is schematically shown installed in a fluid control circuit of the type used during a cardiopulmonary surgical procedure. In particular, a first end of a first suction tube 12 is shown inserted into a left ventricle 16 of a patient's heart 18. The second end of first suction tube 12 is connected to an inlet section 20 of control valve assembly 10. A first end of a second suction tube 22 is shown connected to an outlet section 24 of control valve assembly 20. A cardiotomy reservoir 26 is shown connected to the second end of second suction tube 22. As seen, a roller-type of positive displacement aspiration pump 28 includes a roller member which rolls along second suction tube 22 to create a vacuum in first suction tube 12. Thus, blood which has accumulated in left ventricle 16 of heart 18 is drawn through first suction tube 12 and control valve assembly 10 into second suction tube 22 from where it is transferred into cardiotomy reservoir 26. As is understood, the blood and other fluids collected in cardiotomy reservoir 26 are typically filtered and otherwise treated prior to being reintroduced into the patient's circulatory system.

With particular reference now to FIGS. 2 through 6, a preferred construction for control valve assembly 10 will now be described. Control valve assembly 10 is shown to include a two-piece housing assembly 30 comprised of tubular inlet housing 20 and tubular outlet housing 24. Inlet housing 20 includes an axial connector segment 32 having external barbs 34 formed thereon and which defines an axial inlet passage 36. Connector segment 32 is adapted for installation within the open second end of first suction tube 12 with barbs 34 provided to assist in maintaining the connection. Inlet housing 20 also includes a cup-shaped rim segment 38 which extends from connector segment 32. Outlet housing 24 includes an axial connector segment 40 having external barbs 42 formed thereon, and a valvebody segment 44 which terminates with a radial flange 46. Connector segment 40 is adapted for installation into the open first end of second suction tube 22 with barbs 42 provided to assist in maintaining the connection. As seen, connector segment 40 and valvebody segment 44 define a common axial outlet passage 48.

Upon assembly of housing assembly 30, flange 46 is retained within rim segment 38 such that inlet passage 36 and outlet passage 48 are axially aligned along a common flow axis, as denoted by line "A".

Control valve assembly 10 is equipped with a multi-function valving arrangement which includes an unidirectional flow valve, hereinafter referred to as duckbill valve 50. Duckbill valve 50 is operable to permit fluid flow from inlet passage 36 to outlet passage 48 while preventing fluid flow in the opposite direction from outlet passage 48 to inlet passage 36. Duckbill valve 50 is made of a elastomeric material and includes a cylindrical base segment 52 having a radial mounting rim 54, and a pair of flap segments 56 extending from base segment 52. Flap segments 56 are elastically yieldable and sealingly cooperate with one another along a seal line 58. As seen, mounting rim 54 is retained (i.e., sandwiched) in a complimentary channel formed between rim segment 38 of inlet housing 20 and radial flange 46 of outlet housing 24 to provide a fluid-tight seal therebetween. During surgery, pump 28 generates a negative pressure condition in outlet passage 48 which causes flap segments 56 to separate, thereby establishing a flow aperture along seal line 58 for placing inlet passage 36 in communication with outlet passage 48. As such, blood is drawn from left ventricle 16 of heart 18 through first suction tube 12 into inlet passage 36 of inlet housing 20 and into a valve chamber 60 within duckbill valve 50. Thereafter, the blood flows from valve chamber 60 through the aperture defined between the separated flap segments 52 of duckbill valve 50 into outlet passage 48 of outlet housing 24 from where it is sent through second suction tube 22 to reservoir 26. However, if for some reason pump 28 is inadvertently operated such that a backflow condition is created, the resulting back pressure in outlet passage 48 would cause flap segments 52 to close along seal line 58, thereby preventing reverse flow of fluid back into heart 18. Thus, duckbill valve 50 is a check valve which provides a unidirectional flow control function.

Valvebody segment 44 of outlet housing 24 is shown to include a first cylindrical boss 62 and a second cylindrical boss 64, both of which extend outwardly therefrom. Preferably, bosses 62 and 64 are axially aligned along a common vent axis, as denoted by line "B", which is generally perpendicular to flow axis A. First boss 62 defines an overpressure chamber 66 which communicates with the ambient environment. An aperture 68 and a plurality of vent ports 70 are formed in a flange 72 which separates overpressure chamber 66 from outlet passage 48. Control valve assembly 10 is equipped with a positive pressure (i.e., "overpressure") relief valve, hereinafter referred to as poppet valve 74. Poppet valve 74 includes a shaft portion 74a which is retained in aperture 68, and a head portion 74b which is sized to overlie vent ports 70. Poppet valve 74 is normally located in a "closed" position with head portion 74b covering vent ports 70 to prevent communication between outlet passage 48 and overpressure chamber 66. Poppet valve 74 is maintained in its closed position until the pressure in outlet passage 48 exceeds a predetermined maximum positive pressure value. Once the pressure in outlet passage 48 exceeds this predetermined positive pressure value, poppet valve 74 moves to an "open" position whereat head portion 74b is displaced from vent ports 70. With poppet valve 74 in its open position, a first flow pathway is established for venting pressure from outlet passage 48 to ambient, thereby preventing excessive pressure buildups in second suction tube 22 between pump 28 and control valve assembly 10. Preferably, aperture 68 is centered on vent axis B with vent ports 70 equidistantly spaced and circumferentially arranged to surround aperture 68.

Control valve assembly 10 further includes a negative pressure relief valve, hereinafter referred to as vacuum relief valve 76, which is operable to limit the vacuum level within outlet passage 48 to a preselected maximum negative pressure value by permitting ambient air to be introduced through a vacuum port 78 into outlet passage 48, thereby controlling the rate of aspiration. As will be further detailed, vacuum relief valve 76 is adjustable to permit fine adjustment of the maximum negative pressure value for optimized aspiration control. Vacuum relief valve 76 is shown to include a valve housing 80 mounted in a suction chamber 82 defined by second boss 64 and having suction ports 84, a valve member 86 supported from valve housing 80 for movement between a "closed" position (FIG. 3) and an "open" position (FIG. 4), an end cap 88 mounted to valve member 86, and a bias spring 90 acting between valve housing 80 and end cap 88 for normally urging valve member 86 toward its closed position. With valve member 86 in its closed position, the flow of ambient air through suction ports 84 into suction chamber 82 is prevented. In contrast, movement of valve member 86 to its open position, in opposition to the preload exerted by bias spring 90, establishes a second flow pathway such that ambient air is drawn through suction ports 84, suction chamber 82 and vacuum port 78 into outlet passage 48.

In operation, valve member 86 moves from its closed position to its open position when the vacuum level in outlet passage 48 exceeds a predetermined maximum negative pressure value. Specifically, valve member 86 moves to its open position once the negative pressure acting on valve member 86 within suction chamber 82 overcomes the preload exerted thereon by biasing spring 90. As will be detailed, the preload exerted by bias spring 90 can be adjustably varied for permitting fine adjustment of the maximum negative pressure value at which valve member 86 moves to its open position for providing increased control over the desired aspiration rate. The valve member 86 automatically returns to its closed position when the vacuum level in outlet passage 48 falls below the maximum negative pressure value.

Valve housing 80 is shown to include a first tubular segment 92 and a second tubular segment 94 interconnected by a transverse plate segment 96. Plate segment 96 has a central circular aperture 98 formed therethrough with a set of keyways 100 extending radially therefrom. As best seen from FIG. 6, suction ports 84 also extend through plate segment 94 and surround aperture 98. First tubular segment 92 is rigidly secured within second boss 64 to cooperatively define suction chamber 82. Valve member 86 has a shank segment 102 and a head segment 104. Shank segment 102 includes a non-threaded portion 106 proximal to head segment 104 and an externally threaded portion 108. Non-threaded portion 106 of shank segment 102 is slidingly mounted to extend through aperture 98 and has longitudinal keys 110 which are retained in keyways 100. Retention of keys 110 in keyways 100 acts as an anti-rotation feature which prevents rotation of valve member 86 relative to valve housing 80 while still permitting sliding movement of valve member 86 between its closed and open positions. A seal member, such as an O-ring seal 112, is shown mounted on non-threaded portion 106 of shank segment 102 adjacent to head segment 104. Seal 112 is operable to overlie and cover suction ports 84 when valve member 86 is in its closed position.

End cap 88 includes a base segment 116, an annular spring guide segment 118, and a skirt segment 120. A threaded aperture 122 is formed through base segment 116 and spring guide segment 118 such that end cap 88 is threaded onto threaded portion 108 of shank segment 102. Bias spring 90 is shown as a coil spring concentrically mounted to surround threaded portion 108 of shank segment 102 with one end retained within second tubular segment 94 and engaging plate segment 96 of valve housing 80 and its opposite end encircling spring guide segment 118 and engaging base segment 116 of end cap 88. Thus, the threaded position of end cap 88 on shank segment 102 of valve member 86 acts to determine the spring length dimension "D" which, in turn, defines the compressed condition of bias spring 90 for establishing the preload exerted by spring 90 on valve member 86. Skirt segment 120 of end cap 88 encircles valve housing 80 and has an open end with a diameter approximately equal to that of second boss 64. Thus, an annular suction inlet is defined at the open end of end cap 88 between the inner surface of skirt segment 120 and the outer surface of valve housing 80 to permit ambient air to be drawn into a cap chamber 124 for communication with suction ports 84.

During surgery, vacuum relief valve 72 functions to control the aspiration rate by setting the maximum negative pressure value. As noted, the preload exerted on valve member 86 by spring 90 determines this maximum negative pressure value. As shown in FIG. 3, valve member 86 is held by spring 90 in its closed position for preventing communication between cap chamber 124 and suction chamber 82. When a condition occurs that results in the vacuum level in outlet passage 48 exceeding the predetermined negative pressure value, valve member 86 moves to its open position, thereby allowing ambient air to be drawn into cap chamber 124 through suction ports 84 and into suction chamber 82 from where the air is drawn through vacuum port 78 into outlet passage 48. If, at any time during the surgical procedure, it is desired to increase the aspiration rate, end cap 88 is threaded farther onto shank segment 102 for reducing the spring length dimension and further compressing spring 90 which results in a corresponding increase in the preload exerted on valve member 86, thereby increasing the maximum negative pressure value. Conversely, a reduction in the aspiration rate is accomplished by loosening the threaded engagement of end cap 88 on shank segment 102 for reducing the compression of spring 90 which results in a corresponding decrease in the preload exerted on valve member 86, thereby decreasing the maximum negative pressure value. Thus, vacuum relief valve 76 permits fine adjustment of the vacuum pulled through control valve assembly 10 merely by adjusting the rotated position of end cap 88 on valve member 86. Moreover, the vacuum relief function may be rendered inactive by threading end cap 88 onto shank segment 102 until the end of skirt segment 120 impinges upon the edge surface of second boss 64, thereby closing the suction inlet and preventing communication between ambient air and cap chamber 124.

In addition to the fine adjustment control provided by vacuum relief valve 76, it can also be selectively manipulated during surgery to provide a "dump" feature and a "full vacuum" feature. In particular, the dump feature is provided by pushing on end cap 88 to axially move valve member 86 from its closed position to its open position. In contrast, the full vacuum feature is provided by pulling on end cap 88 to physically hold seal 112 against suction ports 84, thereby holding valve member 86 in its closed position regardless of the suction level in outlet passage 48.

Referring now to FIG. 7, a modified vacuum relief valve 76' is shown which is generally similar to vacuum relief valve 76 of FIG. 6 with the exception that suction ports 84 have been eliminated and replaced by suction ports 84' defined by clearance between keys 110 in keyways 100. Thus, when valve member 86 is in its closed position, the flow of ambient air through suction ports 84' into suction chamber 82 is prevented. In contrast, movement of valve member 86 to its open position establishes the second flow pathway such that ambient air is drawn through cap chamber 124, suction ports 84', suction chamber 82 and vacuum port 78 into outlet passage. Obviously, a combination of suction ports 84 and 84' can be used in a further alternative construction if so desired.

The foregoing discussion discloses and describes an exemplary embodiment of the present invention. One skilled in the art will readily recognize from such discussion, and from the accompanying drawings and claims, that various changes, modifications and variations can be made therein without departing from the true spirit and fair scope of the invention as defined in the following claims.

What is claimed is:

1. A multi-function medical control valve comprising;
    a housing assembly including an inlet housing defining an inlet passage and an outlet housing defining an outlet passage;
    a unidirectional flow valve mounted in said housing assembly and operable to only permit fluid to flow from said inlet passage into said outlet passage;
    a positive pressure relief valve supported from said outlet housing and operable to vent pressure from said outlet passage to ambient when the pressure in said outlet passage exceeds a predetermined maximum positive pressure value; and
    a negative pressure relief valve supported from said outlet housing and operable to draw ambient air though a flow path into said outlet passage when the pressure in said outlet passage exceeds a predetermined maximum negative pressure value, said negative pressure relief valve including a valve member movable between a closed position preventing air flow through said flow path and an open position permitting air flow through said flow path, a spring exerting a preload on said valve member for urging said valve member toward its closed position, and
    an end cap secured to a shank segment of said valve member for acting on said valve member for selectively varying the preload exerted by said spring on said valve member by adjusting a position of said end cap relative to said valve member to thereby cause a corresponding change in said predetermined maximum negative pressure value.

2. The multi-function medical control valve of claim 1 wherein said end cap is threaded onto said shrank segment of said valve member.

3. The multi-function medical control valve of claim 2 wherein said negative pressure relief valve further includes a valve housing fixed to said outlet housing and defining a suction chamber which communicates with said outlet passage, said flow path including a suction port which extends through said valve housing and communicates with said suction chamber, wherein said valve member has a head segment located in said suction chamber and a shank segment which is supported for sliding movement relative to said valve housing, said end cap is secured to said shank segment of said valve member and said spring is disposed between said end cap and said valve housing for normally biasing said valve member to its closed position whereat said head segment covers said suction port, whereby selective adjustment of the position of said end cap on said shank segment varies the preload exerted on said valve member.

4. The multi-function medical control valve of claim 3 wherein said valve housing includes a tubular segment fixed in a boss extending outwardly from said outlet housing, and a plate segment closing one end of said first tubular segment, said plate segment including an aperture through which said shank segment of valve member extends, and wherein said suction port is formed through said plate segment.

5. The multi-function medical control valve of claim 4 wherein said end cap is threaded onto a threaded portion of said shank segment and includes a skirt segment encircling said valve housing such that an open end of said skirt segment defines an annular suction inlet which permits ambient air to flow into a cap chamber within said end cap and communicate with said suction port.

6. The multi-function medical control valve of claim 5 further including keyways formed in said plate segment which communicate with said aperture and keys projecting from said shank segment of said valve member which are disposed in said keyways to prevent rotation of said valve member relative to said valve housing.

7. The multi-function medical control valve of claim 1 wherein said flow path includes a suction chamber formed in a boss extending from said outlet housing and a vacuum port extending between said suction chamber and said outlet passage, said flow path further includes a suction port formed in a valve housing which encloses said suction chamber with said suction port providing communication between ambient air and said suction chamber, and wherein said valve member is supported by said valve housing for movement between its closed position whereat said suction port is closed and its open position whereat said suction port is open.

8. The multi-function medical control valve of claim 7 wherein said adjustment member is secured to said valve member and said spring acts between said adjustment member and said valve housing to bias said valve member to its closed position, said adjustment member being selectively positionable on said valve member to change the preload exerted by said spring for causing a corresponding change in said predetermined maximum negative pressure value.

9. The multi-function medical control valve of claim 8 wherein said valve member includes a head segment overlying said suction port and a shank segment support for sliding movement relative to said valve housing, and wherein said adjustment member is an end cap that is threaded onto a threaded portion of said shank segment such that rotation of said end cap causes a change in the relative axial position between said end cap and said valve housing which changes the preload of said spring.

10. The multi-function medical control valve of claim 9 wherein said spring is a coil spring concentrically mounted on said shank segment of said valve member and which has a first end acting on said valve housing and a second end acting on said end cap.

11. A multi-function medical control valve comprising:
a housing assembly including an inlet housing defining an inlet passage and an outlet housing defining an outlet passage;
a unidirectional flow valve mounted in said housing assembly and operable to only permit fluid to flow from said inlet passage into said outlet passage;
a positive pressure relief valve supported from said outlet housing and operable to vent pressure from said outlet passage to ambient when the pressure in said outlet passage exceeds a predetermined maximum positive pressure value; and
a negative pressure relief valve supported from said outlet housing and operable to draw ambient air into said outlet passage when the pressure in said outlet passage exceeds a predetermined maximum negative pressure value, said negative pressure relief valve includes a valve housing fixed to said outlet housing and defining a suction chamber which communicates with said outlet passage, and a valve member having a head segment disposed in said suction chamber and a shank segment extending through an aperture formed in said valve housing, said negative pressure relief valve further including an end cap movably retained on said shank segment, and a spring acting between said end cap and said valve housing, said spring acting to bias said head segment to a closed position covering a suction port formed through said valve housing to prevent ambient air from being drawn into said suction chamber, and wherein the relative position of said end cap on said shank segment establishes the preload exerted on said valve member such that a selective change in the relative position of said end cap on said shank segment causes a corresponding change in the preload for adjusting the predetermined maximum negative pressure value.

12. The multi-function medical control valve of claim 11 wherein said end cap is threaded onto a threaded portion of said shank segment and includes a skirt segment encircling said valve housing such that an open end of said skirt segment defines an annular suction inlet which permits ambient air to communicate with said suction port.

13. The multi-function medical control valve of claim 11 further including keyways formed in said valve housing which communicate with said aperture and keys projecting from said shank segment which are disposed in said keyways to prevent rotation of said valve member relative to said valve housing.

14. A multifunction medical control valve comprising:
a housing assembly including an inlet housing defining an inlet passage and an outlet housing defining an outlet passage;
a unidirectional flow valve mounted in said housing assembly and operable to permit fluid to flow from said inlet passage toward said outlet passage;
a positive pressure relief valve operatively engaged to said outlet passage and operable to vent pressure from said outlet passage to ambient when the pressure in said outlet passage exceeds a predetermined maximum positive pressure value; and
a negative pressure relief valve operably associated with said outlet passage and operable to draw air through a flowpath into said outlet passage when the pressure in said outlet passage exceeds a predetermined maximum negative pressure value, said negative pressure relief valve including a valve member movable between a closed position preventing airflow through said flowpath and an open position for admitting airflow through said flowpath, a spring exerting a preload on said valve member for urging said valve member towards its closed position, and
an end cap secured to a shank segment of said valve member for acting on said valve member for the operator during use of the valve to selectively vary the preload exerted by said spring on said valve member by adjusting a position of said end cap relative to said valve member to thereby cause a corresponding change in said predetermined negative pressure valve.

* * * * *